(12) United States Patent
Wada (10) Patent No.: US 9,724,246 B2
(45) Date of Patent: Aug. 8, 2017

(54) DEVICE FOR CONVEYING ABSORBENT ARTICLE AND CONVEYANCE METHOD USING SAME

(71) Applicant: ZUIKO CORPORATION, Osaka (JP)

(72) Inventor: Takao Wada, Osaka (JP)

(73) Assignee: Zuiko Corporation (JP)

( * ) Notice: Subject to any disclaimer, the term of this patent is extended or adjusted under 35 U.S.C. 154(b) by 0 days.

(21) Appl. No.: 15/030,619

(22) PCT Filed: Oct. 21, 2014

(86) PCT No.: PCT/JP2014/077986
§ 371 (c)(1),
(2) Date: Apr. 20, 2016

(87) PCT Pub. No.: WO2015/068567
PCT Pub. Date: May 14, 2015

(65) Prior Publication Data
US 2016/0250080 A1 Sep. 1, 2016

(30) Foreign Application Priority Data
Nov. 11, 2013 (JP) .................................. 2013-233008

(51) Int. Cl.
*B65G 47/64* (2006.01)
*B65G 47/52* (2006.01)
(Continued)

(52) U.S. Cl.
CPC .. *A61F 13/15764* (2013.01); *A61F 13/15772* (2013.01); *B65G 47/64* (2013.01);
(Continued)

(58) Field of Classification Search
None
See application file for complete search history.

(56) References Cited

U.S. PATENT DOCUMENTS 4,307,800 A 12/1981 Joa
7,617,656 B2 * 11/2009 Wiedmann ........ A61F 13/15747
493/12

(Continued)

FOREIGN PATENT DOCUMENTS

EP 0030653 A2 6/1981
EP 2316766 A2 5/2011
(Continued)

OTHER PUBLICATIONS

International Search Report.
European Search Report Dated Sep. 9, 2016.

*Primary Examiner* — Kavel Singh
(74) *Attorney, Agent, or Firm* — Gerald E. Hespos; Michael J. Porco; Matthew T. Hespos (57) ABSTRACT

It is aimed to provide a conveying device for absorbent articles capable of precisely sorting an absorbent article between a main conveyance path and a branch path and a conveyance method using the same. A path switching means includes a belt conveying unit with a conveying belt arranged along an annular path and configured to circulate along the annular path to be able to convey an absorbent article and a path switching mechanism configured to switch a conveyance path specified by the conveying belt between a path along which the absorbent article is transferrable from an upstream conveying mechanism to a downstream conveying mechanism and a path along which the absorbent article is guided along a sampling path from the upstream conveying mechanism.

3 Claims, 6 Drawing Sheets

(51) Int. Cl.
*B65G 47/71* (2006.01)
*B65H 29/12* (2006.01)
*B65H 29/62* (2006.01)
*A61F 13/15* (2006.01)
*B65H 29/58* (2006.01)
*B65H 29/24* (2006.01)

(52) U.S. Cl.
CPC ........... B65H 29/12 (2013.01); B65H 29/242 (2013.01); B65H 29/58 (2013.01); B65H 29/585 (2013.01); B65H 29/62 (2013.01); *B65H 2301/4461* (2013.01); *B65H 2301/4474* (2013.01); *B65H 2404/2613* (2013.01); *B65H 2404/2693* (2013.01)

(56) References Cited

U.S. PATENT DOCUMENTS

| | | | |
|---|---|---|---|
| 9,096,405 B2 * | 8/2015 | Nakano | B65G 47/647 |
| 2013/0001042 A1 | 1/2013 | Yamamoto | |
| 2013/0062263 A1 | 3/2013 | Nakano | |
| 2013/0180835 A1 | 7/2013 | Ishikawa et al. | |

FOREIGN PATENT DOCUMENTS

| | | |
|---|---|---|
| EP | 2554278 A1 | 2/2013 |
| JP | 1-252457 | 10/1989 |
| JP | 5-178452 | 7/1993 |
| JP | 2006-96520 | 4/2006 |
| JP | 2011-140392 | 7/2011 |
| JP | 2012-75627 | 4/2012 |

* cited by examiner

DEVICE FOR CONVEYING ABSORBENT ARTICLE AND CONVEYANCE METHOD USING SAME

TECHNICAL FIELD

The present invention relates to a device for conveying an absorbent article and a conveyance method using the same.

BACKGROUND ART

Conventionally, there has been known a device for conveying absorbent articles such as disposable diapers and sanitary napkins.

The conveying device of this type is configured to be switchable between a state where absorbent articles are conveyed along a main conveyance path set in advance and a state where the absorbent articles are conveyed along a branch conveyance path branched off from the main conveyance path.

For example, a sorting device described in Japanese Unexamined Patent Publication No. 2012-75627 includes an upstream conveying mechanism for conveying an absorbent article, a downstream conveying mechanism provided downstream of the upstream conveying mechanism on the main conveyance path and a sorting mechanism for guiding the absorbent article to the branch conveyance path in the process of transferring the absorbent article from the upstream conveying mechanism to the downstream conveying mechanism.

The sorting mechanism includes a sorting member formed to intersect with a main conveyance path in a state rotated within a predetermined rotation range about an axis of rotation parallel to the main conveyance path and escape from the main conveyance path in a state rotated within a rotation range other than the former rotation range, and a rotating device for rotating the sorting member.

In the case of guiding the absorbent article to the branch conveyance path in this sorting device, the sorting member starts rotating to intersect with the main conveyance path and rotates to have a speed substantially equal to a conveying speed of the absorbent article with the sorting member and the absorbent article held in contact.

Here, an angular speed of the sorting member rotating about the axis of rotation differs according to a distance (radius) from the axis of rotation.

Thus, a speed difference is created between the absorbent article and the sorting member with the sorting member and the absorbent article held in contact.

In addition, since the rotation and stop of the sorting member are repeated according to whether or not sorting is necessary in the sorting mechanism, it is difficult to suddenly accelerate the sorting member from a stopped state in accordance with the speed of the absorbent article. Also in this respect, a speed difference may be created between the absorbent article and the sorting member.

Since the absorbent article is subject to friction resistance with the sorting member or the upstream conveying mechanism according to the aforementioned speed difference, this frictional resistance acts as a braking force and it may not be possible to precisely sort the absorbent article.

SUMMARY OF INVENTION

The present invention aims to provide a device for conveying an absorbent article which device can precisely sort the absorbent article between a main conveyance path and a branch path and a conveyance method using the same.

To solve the above problem, the present invention provides a conveying device switchable between a state where an absorbent article is conveyed along a main conveyance path set in advance and a state where the absorbent article is conveyed along a branch conveyance path branched off from the main conveyance path, the conveying device including an upstream conveying mechanism provided on the main conveyance path and configured to convey the absorbent article, a downstream conveying mechanism provided downstream of the upstream conveying mechanism on the main conveyance path and configured to convey the absorbent article, and a path switching means configured to switch a conveyance path of the absorbent article to guide the absorbent article to the branch conveyance path in the process of transferring the absorbent article from the upstream conveying mechanism to the downstream conveying mechanism, the path switching means including a belt conveying unit with a conveying belt arranged along an annular path and configured to circulate along the annular path so as to be able to convey the absorbent article and a path switching mechanism configured to switch a conveyance path specified by the conveying belt between a path along which the absorbent article is transferrable from the upstream conveying mechanism to the downstream conveying mechanism and a path along which the absorbent article is guided along the branch conveyance path from the upstream conveying mechanism.

Further, the present invention provides a conveyance method for conveying an absorbent article using the above conveying device, the conveyance method including a main conveyance step of conveying the absorbent article along a main conveyance path set in advance, and a branch conveyance step of conveying the absorbent article along a branch conveyance path branched off from the main conveyance path, a conveyance path specified by the conveying belt being set to be able to transfer the absorbent article from the upstream conveying mechanism to the downstream conveying mechanism with the conveying belt kept circulating in the main conveyance step, and the conveyance path specified by the conveying belt being set to guide the absorbent article along the branch conveyance path from the upstream conveying mechanism with the conveying belt kept circulating in the branch conveyance step.

According to the present invention, it is possible to precisely sort an absorbent article between a main conveyance path and a branch path.

DESCRIPTION OF EMBODIMENT

Hereinafter, embodiments of the present invention are described with reference to the accompanying drawings. Note that the following embodiments are specific examples of the present invention and not of the nature to limit the technical scope of the present invention.

First Embodiment

Figure 1:
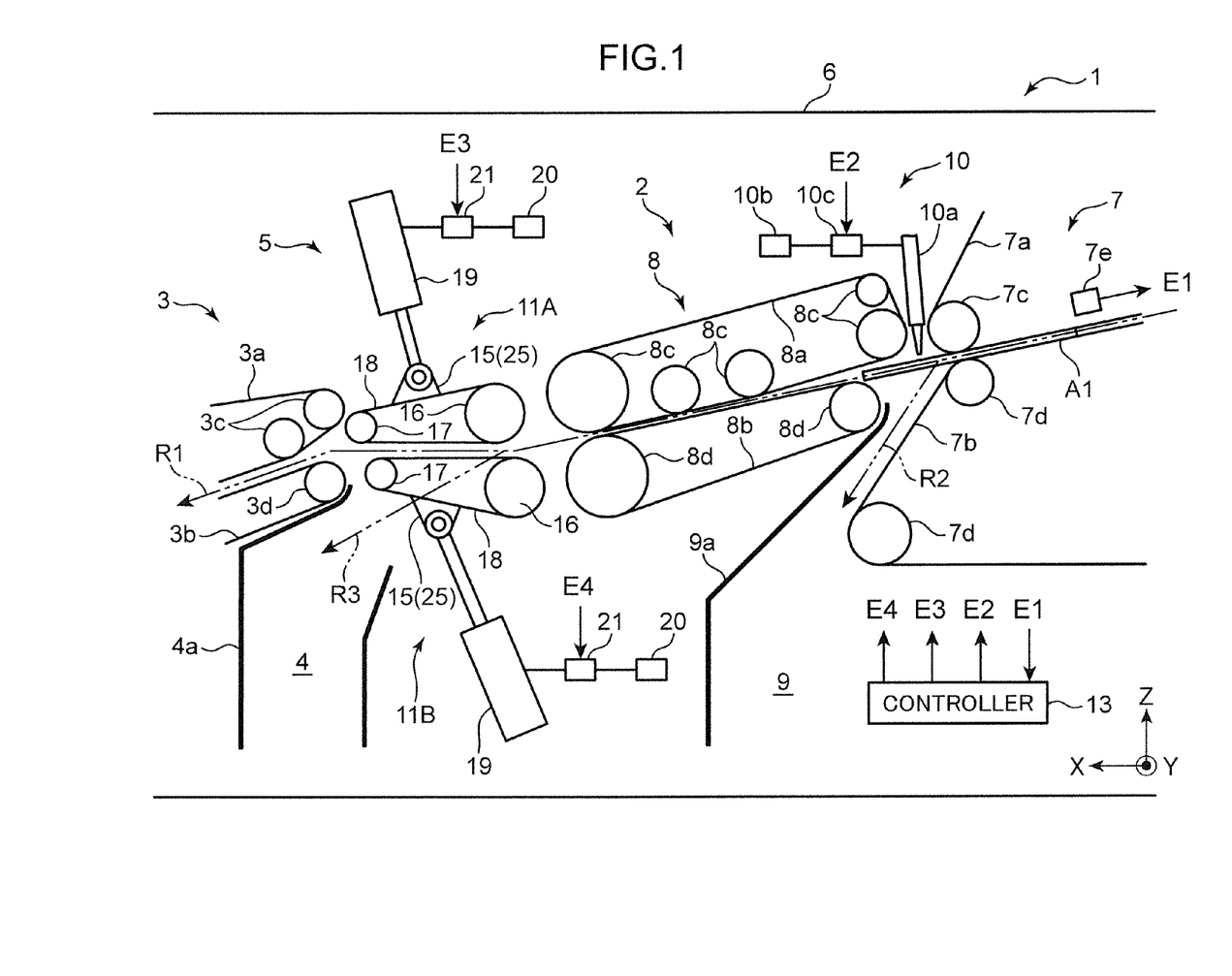
FIG. 1 is a side schematic view showing an overall configuration of a conveying device according to a first embodiment of the present invention.

With reference to FIG. 1, a conveying device 1 according to a first embodiment is switchable among a state where absorbent articles A1 are conveyed along a main conveyance path R1 set in advance, a state where the absorbent articles A1 are conveyed along a defective article collection path R2 branched off from the main conveyance path R1 and a state where the absorbent articles A1 are conveyed along a sampling path (branch conveyance path) R3 branched off from the main conveyance path R1.

Here, the absorbent articles A1 include disposable diapers and sanitary napkins.

Hereinafter, a specific configuration of the conveying device 1 is described with a direction orthogonal to the plane of FIG. 1 as a Y direction, an upward or downward direction of FIG. 1 as a Z direction and a direction orthogonal to the Y and Z directions as an X direction.

The conveying device 1 includes an upstream conveying mechanism 2 provided on the main conveyance path R1 and configured to convey the absorbent article A1, a downstream conveying mechanism 3 provided downstream of the upstream conveying mechanism 2 on the main conveyance path R1 and configured to convey the absorbent article A1, a path switching means 5 provided between the upstream conveying mechanism 2 and downstream conveying mechanism 3 on the main conveyance path R1, a good article sampling unit 4 provided on the sampling path R3, a supporting unit 6 configured to support the both conveying mechanisms 2, 3 and the path switching means 5 on one side in the Y direction (back side of FIG. 1) and a controller 13 configured to control the drive of the path switching means 5.

The upstream conveying mechanism 2 includes a first conveying unit 7 provided upstream of the defective article collection path R2 on the main conveyance path R1, a second conveying unit 8 provided downstream of the defective article collection path R2 on the main conveyance path R1, a defective article collecting unit 9 provided downstream of the defective article collection path R2 and a defective article sorting unit 10 configured to guide the absorbent article A1 judged to be a defective article to the defective article collection path R2.

The conveying unit 7 includes a pair of conveying belts 7a, 7b, a plurality of pulleys 7c, 7d (only some are shown in FIG. 1) allowing the conveying belts 7a, 7b to be respectively provided thereon along annular paths (only parts are shown in FIG. 1) such that parts of the both conveying belts 7a, 7b face each other across the main conveyance path R1, and an imaging means 7e for imaging the absorbent article A1 being conveyed along the main conveyance path R1.

The first conveying unit 7 conveys the absorbent article A1 along the main conveyance path R1 with the absorbent article A1 sandwiched between the parts of the both conveying belts 7a, 7b facing each other by circulatory movements of the both conveying belts 7a, 7b.

The imaging means 7e partly or entirely images the absorbent article A1 conveyed to an imaging range thereof and outputs imaged data E1 to the controller 13. The imaged data E1 is used to discriminate whether or not the absorbent article A1 is a defective article and discriminate the passage (presence) of the absorbent article A1 in the controller 13.

Note that a means for obtaining information for discriminating whether or not the absorbent article A1 is defective is not limited to the imaging means 7e and, using a sensor capable of detecting the presence or absence of a specific part of the absorbent article A1 or a component used in the production of the absorbent article A1, the controller 13 may discriminate a defect based on whether or not this part is detected. In this case, it is necessary to separately provide a sensor for detecting the passage (presence) of the absorbent article A1.

The second conveying unit 8 includes a pair of conveying belts 8a, 8b and a plurality of pulleys 8c, 8d allowing the conveying belts 8a, 8b to be respectively provided thereon along annular paths such that parts of the both conveying belts 8a, 8b face each other across the main conveyance path R1.

The first conveying unit 8 conveys the absorbent article A1 along the main conveyance path R1 with the absorbent article A1 sandwiched between the parts of the both conveying belts 8a, 8b facing each other by circulatory movements of the both conveying belts 8a, 8b.

The defective article collecting unit 9 includes a slope 9a for causing the absorbent article A1 judged to be a defective article to slide down along the defective article collection path R2.

The defective article sorting unit 10 includes an injection nozzle 10a for injecting air to the absorbent article A1 located between the first conveying unit 7 and the second conveying unit 8, an air source 10b for supply air to the injection nozzle 10a and a valve 10c capable of opening and closing an air passage between the air source 10b and the injection nozzle 10a.

In the defective article sorting unit 10, air is injected from the air source 10b through the injection nozzle 10a by opening the valve 10c according to a command E2 from the controller 13.

In this way, the absorbent article A1 located between the first convey unit 7 and the second conveying unit 8 is blown toward the defective article collection path R2 and guided into the defective article collecting unit 9 along the slope 9a.

The downstream conveying mechanism 3 includes a pair of conveying belts 3a, 3b, a plurality of pulleys 3c, 3d (only some are shown in FIG. 1) allowing the conveying belts 3a, 3b to be respectively provided thereon along annular paths (only parts are shown in FIG. 1) such that parts of the both conveying belts 3a, 3b face each other across the main conveyance path R1.

The downstream conveying unit 3 conveys the absorbent article A1 along the main conveyance path R1 with the absorbent article A1 sandwiched between the parts of the both conveying belts 3a, 3b facing each other by circulatory movements of the both conveying belts 3a, 3b.

The good article sampling unit 4 includes a slope 4a for causing the absorbent article A1 to slide down along the sampling path R3 when the number of the absorbent articles A1 judged to be good articles reaches a preset number.

The path switching means 5 switches a conveyance path of the absorbent article A1 to guide the absorbent article A1 to the sampling path R3 in the process of transferring the absorbent article A1 from the upstream conveying mechanism 2 to the downstream conveying mechanism 3.

Specifically, the path switching means 5 includes a pair of switchable conveyors 11A, 11B provided between the upstream conveying mechanism 2 and the downstream conveying mechanism 3 on the main conveyance path R1.

Since the switchable conveyors 11A, 11B are substantially vertically symmetrically configured with respect to the main conveyance path R1, the configuration of the upper switchable conveyor 11A is mainly described.

Figure 2:
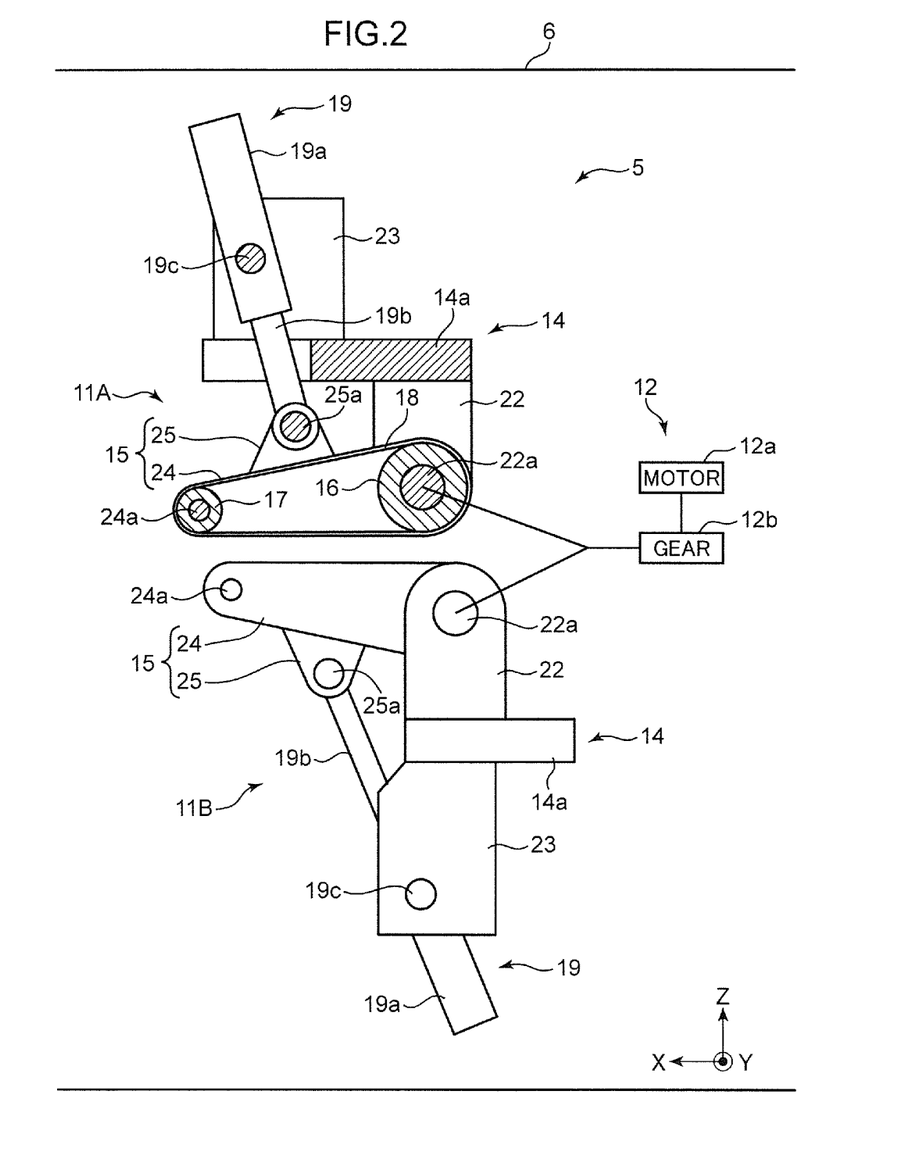
FIG. 2 is a side view enlargedly showing a part of a path switching means of FIG. 1 in section.

FIG. 2 shows a side sectional view of the switchable conveyor 11A and a side view of the switchable conveyor 11B.

With reference to FIG. 2, the switchable conveyor 11A includes a base 14 fixed to the supporting unit 6, a pair of arms 15 rotatably attached to the base 14, a pair of pulleys 16, 17 provided between the both arms 15, a conveying belt 18 provided on the both pulleys 16, 17, a driving unit 12 for driving the conveying belt 18 in a circulating manner, a cylinder 19 for rotating the both arms 15, an air source 20 (see FIG. 1) for supplying air to the cylinder 19 and a valve 21 (see FIG. 1) provided between the cylinder 19 and the air source 20.

In the first embodiment, the driving unit 12, the pulleys 16, 17 and the conveying belt 18 correspond to a belt conveying unit and the base 14, the arms 15, the cylinder 19, the air source 20 and the valve 21 correspond to a path switching mechanism.

The base 14 includes a plate-like part 14a extending in the Y direction from the supporting unit 6, a pair of arm supporting portions 22 extending toward the another switchable conveyor (switchable conveyor 11B) from the plate-like part 14a and facing each other in the Y direction and a pair of cylinder supporting portions 23 extending to a side opposite to the both arm supporting portions 22 from the plate-like part 14a and facing each other in the Y direction.

Each arm 15 includes an arm main body 24 for holding the both pulleys 16, 17 and a cylinder attaching portion 25 having the cylinder 19 attached thereon. The cylinder mounting portion 25 projects toward the cylinder supporting portion 23 from the arm main body 24.

The both arm supporting portions 22 are provided with a shaft 22a extending in the Y direction across the both arm supporting portions 22. Base end parts of the both arm main bodies 24 are attached to the shaft 22a to be rotatable about the shaft 22a between the both arm supporting portions 22. The both arm main bodies 24 and the shaft 22a are relatively rotatable.

Further, the pulley 16 is fixed to a part of the shaft 22a between the both arm main bodies 24. The pulley 16 rotates as the shaft 22a is rotated and driven by the driving unit 12.

Here, the driving unit 12 includes a motor 12a and a gear 12b for distributing power of the motor 12a to the switchable conveyors 11A, 11B. The gear 12b converts a driving direction of the motor 12a such that the pulley 16 of the switchable conveyor 11A and the pulley 16 of the switchable conveyor 11B are driven in opposite directions.

Note that although the common motor 12a is provided for the switchable conveyors 11A, 11B in this embodiment, a motor may be provided for each of the switchable conveyors 11A, 11B. On the other hand, the switchable conveyors 11A, 11B may be driven using a power source common to the upstream conveying mechanism 2 and the downstream conveying mechanism 3.

A shaft 24a extending in the Y direction across the both arm main bodies 24 is provided on tip parts of the both arm main bodies 24. The pulley 17 is rotatably attached to the shaft 24a.

The conveying belt 18 is provided on the pulleys 16, 17 to be arranged along an annular path. A downward facing part of the conveying belt 18 of the switching conveyor 11A and an upward facing part of the conveying belt 18 of the switching conveyor 11B are arranged to face each other.

The cylinder 19 includes a cylinder main body 19a and a rod 19b configured to extend and contract with respect to the cylinder main body 19a as air is supplied to and discharged from the cylinder main body 19a.

The both cylinder mounting portions 25 are provided with a shaft 25a extending in the Y direction across the both cylinder mounting portions 25. A tip part of the rod 19b is attached to the shaft 25a to be rotatable about the shaft 25a between the both cylinder mounting portions 25.

Further, the cylinder 19 is provided with a pair of shafts 19c (only the shaft 19c on a front side is shown in FIG. 2) extending toward opposite sides along the Y direction from an intermediate part of the cylinder main body 19a. Each shaft 19c is rotatably supported on the cylinder supporting portion 23.

Accordingly, by the extension of the rods 19b of the cylinders 19, the both arms 15 rotate downwardly about the shaft 22a while the cylinder 19 is rotating in the switchable conveyor 11A, whereas the both arms 15 rotate upwardly about the shaft 22a while the cylinder 19 is rotating in the switchable conveyor 11B.

When the rod 19b of the cylinder 19 contracts, the both arms 15 of each switchable conveyor 11A, 11B respectively rotate in a direction opposite to the above one.

Figure 3:
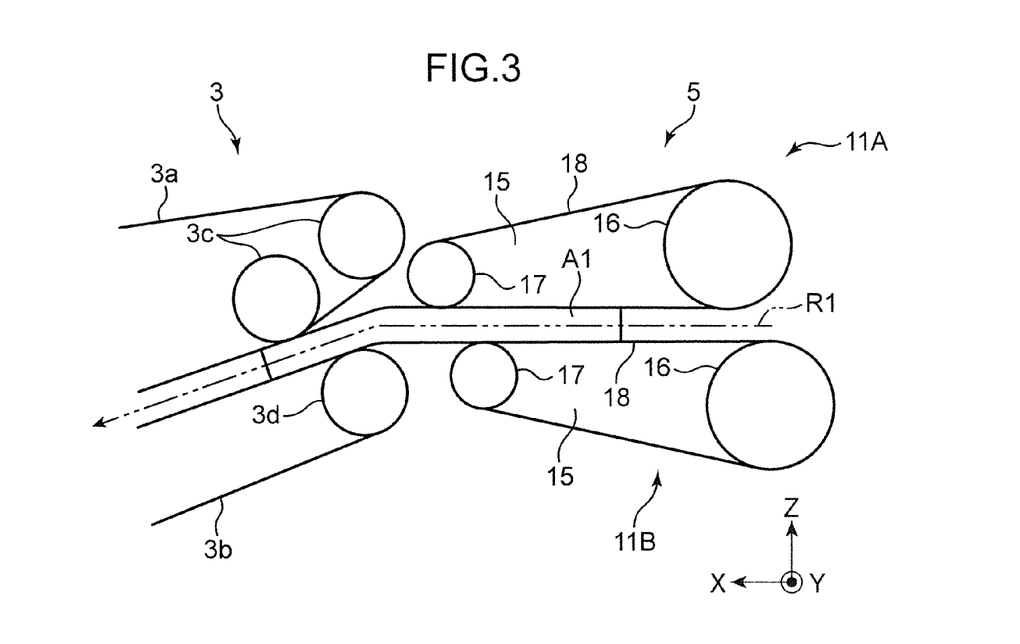
FIG. 3 is a side schematic view showing an operation of the conveying device of FIG. 1 in a state where an absorbent article is conveyed along a main conveyance path.
Figure 4:
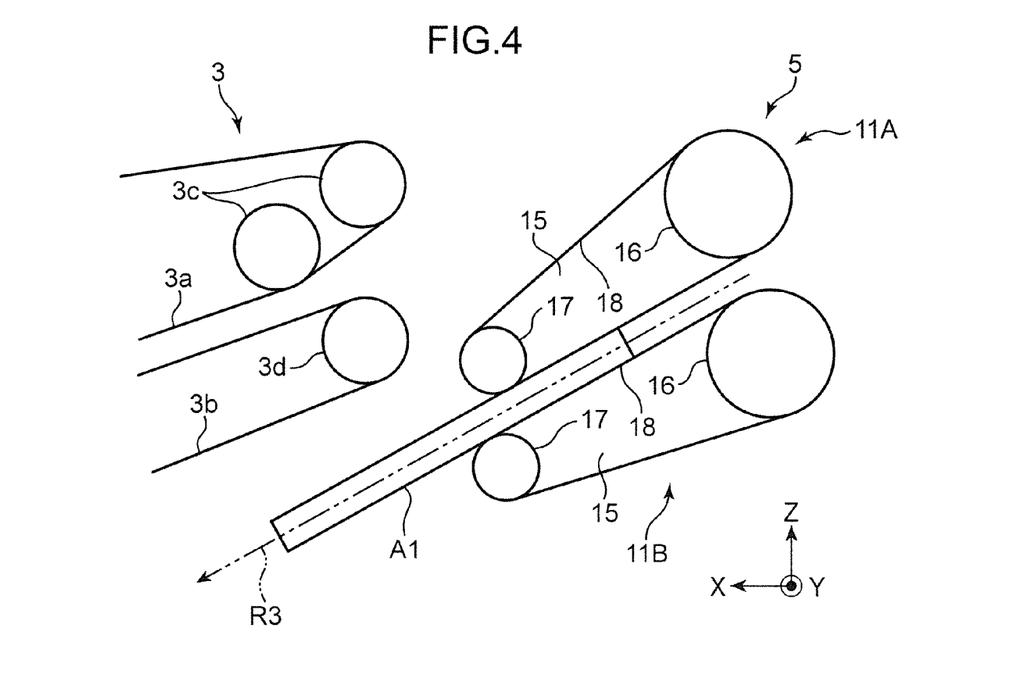
FIG. 4 is a side schematic view showing an operation of the conveying device of FIG. 2 in a state where the absorbent article is conveyed along a branch conveyance path.

By combining movements of the both cylinders 19, directions of the arms 15 of the both switchable conveyors 11A, 11B can be switched between a state where the absorbent article A1 is conveyed along the main conveyance path R1 while being sandwiched between the both conveying belts 18 as shown in FIG. 3 and a state where the absorbent article A1 is conveyed along the sampling path R3 while being sandwiched between the both conveying belts 18 as shown in FIG. 4.

With reference to FIG. 1, the controller 13 controls the operations of the both switchable conveyors 11A, 11B by outputting commands E3, E4 to the valves 21.

Here, by the input of the commands E3, E4, the valves 21 are switchable between a state where air from the air sources 20 is supplied to rod-side chambers of the cylinders 19 and air in head-side chambers of the cylinders 19 is discharged and a state where air from the air sources 20 is supplied to the head-side chambers of the cylinders 19 and air in the rod-side chambers of the cylinders 19 is discharged.

Further, the controller 13 normally outputs the commands E3, E4 for switching the both switchable conveyors 11A, 11B to the state shown in FIG. 3.

Figure 5:
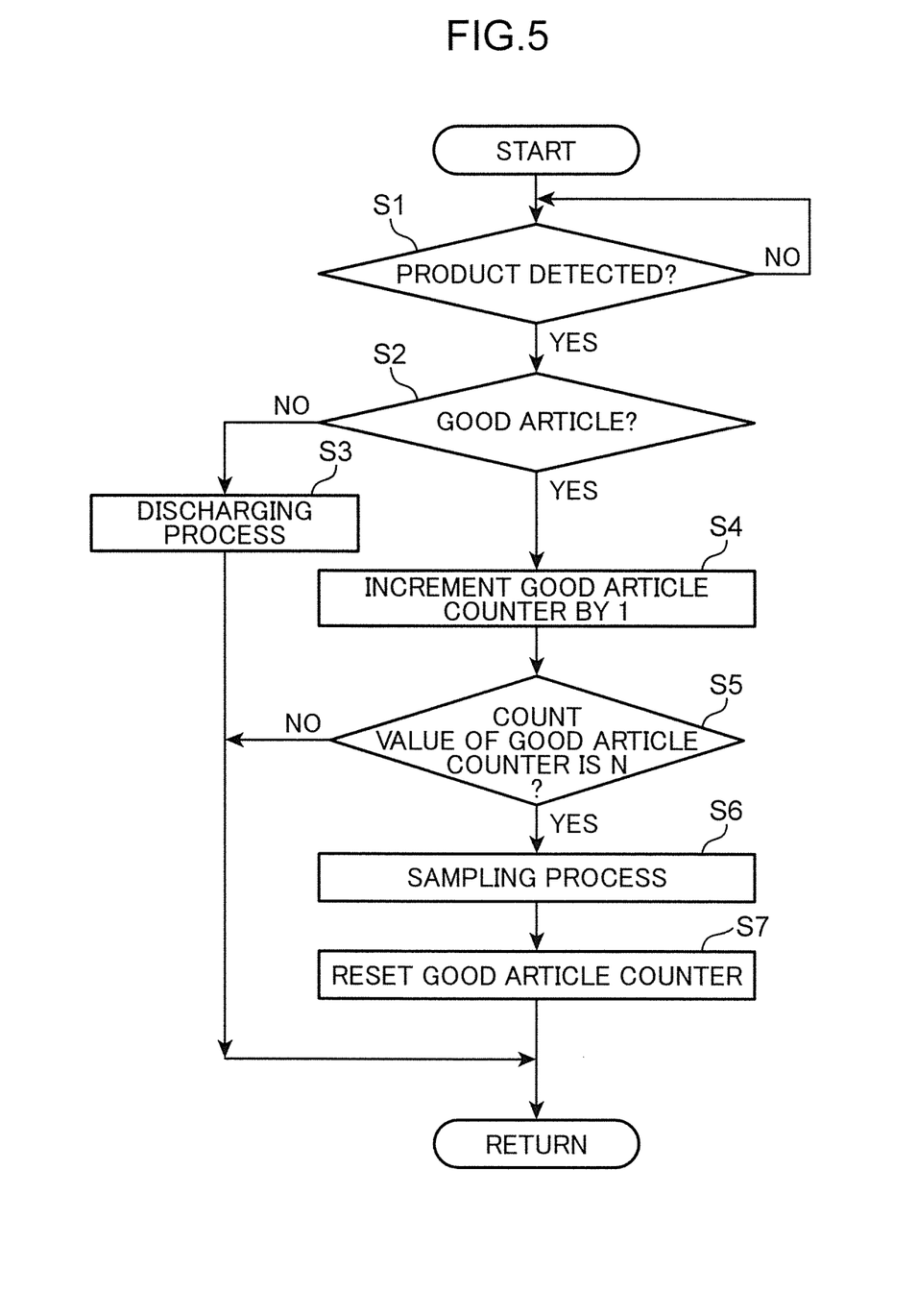
FIG. 5 is a flow chart showing a process performed by a controller of FIG. 1.

A process performed by the controller 13 is described below with reference to FIGS. 1 and 5. Note that the following process is performed with the pulleys 16 of the both switchable conveyors 11A, 11B driven by the motor 12a.

When the process by the controller 13 is started, it is determined whether or not the absorbent article A1 has been detected by the imaging means 7e (Step S1). Here, if it is determined that the absorbent article A1 has not been detected, Step S1 is repeatedly performed.

On the other hand, if it is determined that the absorbent article A1 has been detected, it is determined whether or not this absorbent article A1 satisfies a defect condition set in advance (e.g. whether or not the absorbent article A1 has an improper shape), i.e. whether or not the absorbent article A1 is a good article (Step S2).

Here, a discharging process is performed if the absorbent article A1 is determined to be a defective article (Step S3). Specifically, in the discharging process, the absorbent article A1 is guided to the defective article collecting unit 9 by injecting air by the injection nozzle 10*a*. When the discharging process is finished, a return is made to Step S1.

On the other hand, if the absorbent article A1 is determined to be a good article in Step S2, a good article counter is incremented by 1 (Step S4) and it is determined whether or not the good article counter has reached a number N set in advance (Step S5).

Here, this process returns to Step S1 if the good article counter is determined to have a count value below N, whereas a sampling process is performed if the good article counter is determined to have a count value of N (Step S6).

In the sampling process, the directions of the arms 15 of the both switching conveyors 11A, 11B are switched to convey the absorbent article A1 along the sampling path R3 as shown in FIG. 4 by outputting the commands E3, E4 respectively to the valves 21 of the both switching conveyors 11A, 11B.

The absorbent article A1 conveyed to the good article sampling unit 4 along the sampling path R3 in this way is used, for example, for inspection to confirm a state of products.

When the sampling process is completed, the good article counter is reset to 0 (Step S7) and a return is made to Step S1.

As described above, by switching the conveyance path specified by the conveying belts 18 with the conveying belts 18 kept circulating, a conveyance destination of the absorbent article A1 can be switched between the main conveyance path R1 and the sampling path R3.

Thus, unlike a case where a sorting member is rotated only during conveyance to the branch conveyance path as before, it can be suppressed that a speed difference is created between the conveying belts 18 and the absorbent article A1 during conveyance to the sampling path R3, whereby frictional resistance given to the absorbent article A1 can be reduced.

Accordingly, the absorbent article A1 can be precisely sorted between the main conveyance path R1 and the sampling path R3.

Further, according to the first embodiment, the following effects can be exhibited.

The absorbent article A1 can be conveyed to the main conveyance path R1 or the sampling path R3 while being sandwiched between the pair of conveying belts 18.

Since frictional resistance between the absorbent article A1 and the both conveying belts 18 can be more effectively reduced in this way, the damage of the absorbent article A1 can be prevented.

Further, since the directions of the pair of conveying belts 18 (arms 15) themselves sandwiching the absorbent article A1 are switched, the absorbent article A1 can be reliably conveyed along the main conveyance path R1 or the sampling path R3.

Since the path switching means 5 is provided separately from the defective article sorting unit 10, it is possible to guide the absorbent articles A1, except the defective articles, required to be more carefully handled than the defective articles to the sampling path R3 with frictional resistance suppressed as described above while the defective articles are collected along the defective article collection path R2 by the defective article sorting unit 10.

Since one out of every preset number N of absorbent articles A1 other than the defective articles can be sampled by the controller 13, this absorbent article A1 can be used for inspection to confirm, for example, a state of products.

Second Embodiment

Although the path switching means 5 is provided separately from the upstream conveying mechanism 2 and the downstream conveying mechanism 3 in the first embodiment, an upstream conveying mechanism may be configured to include a path switching means as in a second embodiment described below.

Figure 6:
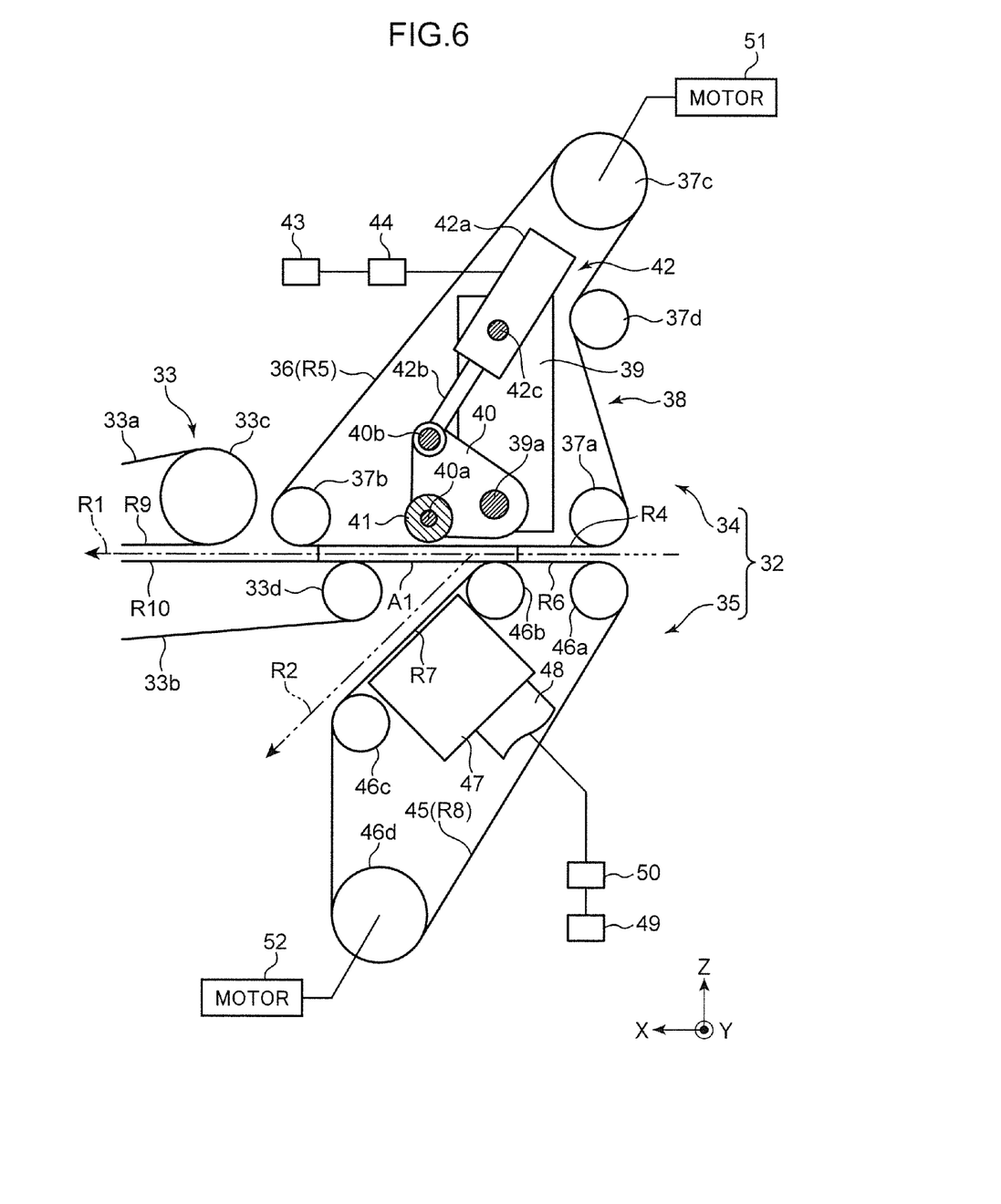
FIG. 6 is a side view enlargedly showing a part of a conveying device according to a second embodiment of the present invention in section.
Figure 7:
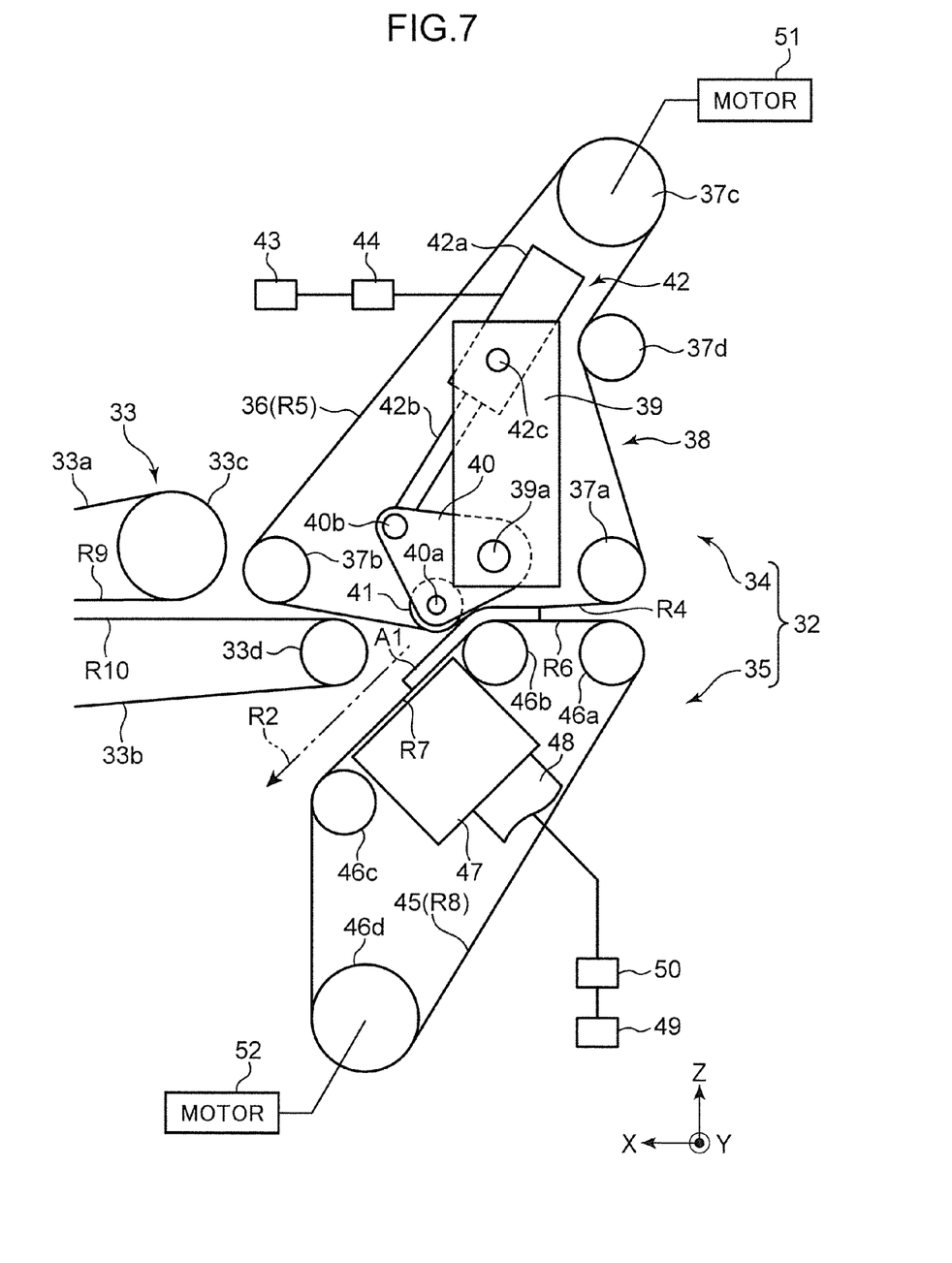
FIG. 7 is a side view showing a state where a path switching means in the conveying device of FIG. 6 is switched.

FIGS. 6 and 7 are side views showing conveying mechanisms of the second embodiment with parts thereof omitted. Note that a side sectional view of a path switching mechanism 38 is shown in FIG. 6.

With reference to FIGS. 6 and 7, a conveying device according to the second embodiment is switchable between a state where an absorbent article A1 is conveyed along a main conveyance path R1 and a state where the absorbent article A1 is conveyed along a defective article collection path (branch conveyance path) R2 branched off from the main conveyance path R1.

Specifically, the conveying device includes an upstream conveying mechanism 32 provided on the main conveyance path R1 and configured to convey the absorbent article A1 and a downstream conveying mechanism 33 provided downstream of the upstream conveying mechanism 32 on the main conveyance path R1 and configured to convey the absorbent article A1.

The upstream conveying mechanism 32 includes a first upstream conveying unit 34 and a second upstream conveying unit 35 arranged in the Z direction across the main conveyance path R1.

The first upper conveying unit 34 includes a path switching means. Specifically, the conveying unit 34 includes a conveying belt 36, a plurality of pulleys 37*a* to 37*d* allowing the conveying belt 36 to be provided thereon along an annular path R5 including a conveying path R4 extending along the main conveyance path R1, the path switching mechanism 38 for switching the annular path R5 and a motor 51 for giving power for circulatory movement to the conveying belt 36.

The conveying belt 36 is circulated in a direction to successively pass the pulleys 37*a*, 37*b*, 37*c* and 37*d* by having power supplied to the pulley 37*c* by the motor 51. A part of the conveying belt 36 between the pulleys 37*a* and 37*b* is set as the conveying path R4. The conveying path R4 is set in a range from an upstream side to a downstream side of a branch point of the main conveyance path R1 to the defective article collection path R2.

The path switching mechanism 38 includes a pair of supporting plates 39 facing each other in the Y direction inside the annular path R5 of the conveying belt 36, a pair of rotary plates 40 rotatably attached to the both supporting plates 39, a pressing pulley (pressing member) 41 rotatably attached to the both rotary plates 40, a cylinder (driving member) 42 for rotating and driving the rotary plates 40, an air source 43 for supplying air to the cylinder 42 and a valve 44 provided between the cylinder 42 and the air source 43.

A shaft 39*a* extending in the Y direction across the both supporting plates 39 is provided on lower end parts of the both supporting plates 39. The both rotary plates 40 have a substantially triangular shape in a side view and one of three corner parts of each of the rotary plates 40 is attached to the shaft 39*a* to be rotatable about the shaft 39*a* between the lower end parts of the both supporting plates 39.

A shaft 40*a* extending in the Y direction across the both rotary plates 40 is provided on the lower one of the remaining two corner parts of each of the both rotary plates 40. The pressing pulley 41 is attached to the shaft 40*a* to be rotatable about the shaft 40*a* between the corner parts of the both rotary plates 40.

The cylinder 42 includes a cylinder main body 42*a* and a rod 42*b* configured to extend and contract with respect to the cylinder main body 42*a* as air is supplied to and discharged from the cylinder main body 42*a*.

A shaft 40*b* extending in the Y direction across the both rotary plates 40 is provided on the remaining one corner part of each of the both rotary plates 40. A tip part of the rod 42*b* is attached to the shaft 40*b* to be rotatable about the shaft 40*b* between the both rotary plates 40.

Further, the cylinder 42 is provided with a pair of shafts 42*c* (only the shaft 42*c* on a front side is shown in FIGS. 6 and 7) extending toward opposite sides along the Y direction from an intermediate part of the cylinder main body 42*a*. Each shaft 42*c* is rotatably supported on an upper part of the supporting plate 39.

As shown in FIG. 6, in a state where the rod 42*b* of the cylinder 42 is contracted, the both rotary plates 40 are pulled upwardly, whereby the pressing pulley 41 is escaped upwardly (into the inside of the annular path R5) from the conveying belt 36.

On the other hand, as shown in FIG. 7, in a state where the rod 42*b* of the cylinder 42 is extended, the cylinder 42 rotates and the both rotary plates 40 rotate downwardly, whereby the pressing pulley 41 presses the conveying belt 36 downwardly from the inside of the annular path R5. As a result, the conveying path R4 specified by the conveying belt 36 is switched as shown in FIG. 7.

Here, the shaft 39*a* is provided upstream of the branch point of the main conveyance path R1 to the defective article collection path R2 and, in the state shown in FIG. 6, the pulley 41 is provided downstream of the branch point of the main conveyance path R1 to the defective article collection path R2.

Thus, by the extension of the rod 42*b* of the cylinder 42, the pulley 41 presses the conveying belt 36 toward the defective article collection path R2 from a position downstream of the branch point of the main conveyance path R1 to the defective article collection path R2.

In this way, the absorbent article A1 can be guided to the defective article collection path R2 while being sandwiched between the conveying belt 36 and a circulating belt 45 of the second upstream conveying unit 35 in the state shown in FIG. 7.

Note that by commands to the valve 44 from an unillustrated controller, the cylinder 42 is normally driven in the state of FIG. 6 and driven in the state of FIG. 7 when the absorbent article A1 is determined to be a defective article.

Since the valve 44 is configured similarly to the valves 21 of the first embodiment, it is not described.

With reference to FIGS. 6 and 7, the second upstream conveying unit 35 conveys the absorbent article A1 between the first and second upstream conveying units 34, 35.

Specifically, the second upstream conveying unit 35 includes the circulating belt 45, a plurality of pulleys 46*a* to 46*d* allowing the circulating belt 45 to be provided thereon along a path for branching R8 including a main path R6 extending along the main conveyance path R1 and a sub path R7 extending along the defective article collection path R2, a suction box 47 for sucking the absorbent article A1 to the circulating belt 45, a suction duct 48 for sucking air in the suction box 47, a suction source 49 connected to the suction duct 48, a valve 50 provided between the suction source 49 and the suction duct 48 and a motor 52 for giving power for circulatory movement to the circulating belt 45.

The circulating belt 45 is circulated in a direction to successively pass the pulleys 46*a*, 46*b*, 46*c* and 46*d* by having power supplied to the pulley 46*d* by the motor 52.

A part of the circulating belt 45 located between the pulleys 46*a* and 46*b* is set as the main path R6. An interval between the circulating belt 45 on the main path R6 and the conveying belt 36 on the conveying path R4 is set to be able to convey the absorbent article A1 along the main conveyance path R1 with the absorbent article A1 sandwiched between the both belts 36 and 45.

Further, a part of the circulating belt 45 located between the pulleys 46*b* and 46*c* is set as the sub path R7. An interval between the circulating belt 45 on the sub path R7 and the conveying belt 36 pressed by the pressing pulley 41 (see FIG. 7) is set to be able to convey the absorbent article A1 to the defective article collection path R2 with the absorbent article A1 sandwiched between the both belts 36 and 45.

The suction box 47 is provided inside the path for branching R8 and sucks air outside the circulating belt 45 through holes formed on the circulating belt 45. In this way, the absorbent article A1 located on the outer side of the circulating belt 45 is sucked to the circulating belt 45.

The valve 50 is switchable between a state where the suction source 49 and the suction duct 48 communicate and a state where the suction source 49 and the suction duct 48 are shut off from each other in response to a command from the unillustrated controller.

The downstream conveying mechanism 33 includes a pair of conveying belts 33*a*, 33*b* and a plurality of pulleys 33*c*, 33*d* (only one each is shown in FIGS. 6 and 7) allowing the conveying belts 33*a*, 33*b* to be respectively provided thereon along annular paths.

A part of the conveying belt 33*a* extending along a path R9 and a part of the conveying belt 33*b* extending along a path R10 are facing each other across the main conveyance path R1. Further, the path R10 extends to a more upstream side than the path R9 and the conveying belt 33*b* located on an upstream part of the path R10 is facing the conveying belt 36 located on a downstream part of the conveying path R4 across the main conveyance path R1.

The operation of the conveying device described above is described below.

If the absorbent article A1 is determined to be a good article, a state where the cylinder 42 is contracted as shown in FIG. 6 is maintained.

This causes the absorbent article A1 to be conveyed along the main conveyance path R1 while being sandwiched between the conveying belt 36 and the circulating belt 45, between the conveying belts 36 and 33*b* and the conveying belts 33*a* and 33*b*.

On the other hand, if the absorbent article A1 is determined to be a defective article, the cylinder 42 extends as shown in FIG. 7.

This causes the conveying belt 36 to be pressed by the pressing pulley 41, thereby switching the path specified by the conveying belt 36. As a result, the absorbent article A1 is guided to the defective article collection path R2 while being sandwiched between the conveying belt 36 and the circulating belt 45.

Here, the valve 50 is opened simultaneously with the extension of the cylinder 42. This causes the absorbent article A1 released from restriction from the conveying belt 36 to be sucked to the circulating belt 45.

As just described, according to the second embodiment, the path specified by the conveying belt 36 of the first upstream conveying unit 34 can be switched between the state where the absorbent article A1 is conveyed along the main conveyance path R1 (main path R6) between the first and second upstream conveying units 34, 35 and the state where the absorbent article A1 is guided to the defective article collection path R2 (sub path R7) between the first and second upstream conveying units 34, 35.

Thus, the configuration of the conveying device can be simplified and a cost reduction caused by this can be realized as compared to the case where the path switching means is provided separately from the upstream and downstream conveying mechanisms 32, 33.

Specifically, the path specified by the conveying belt 36 can be switched by the pressing of the conveying belt 36 by the pressing pulley 41 and the release from this pressing.

Here, if the absorbent article A1 is conveyed at a high speed in the upstream conveying mechanism 32, the absorbent article A1 is conveyed toward the main conveyance path R1 by inertia and it is difficult to convey the absorbent article A1 along the defective article collection path R2 (sub path R7) even if the path specified by the conveying belt 36 of the first upstream conveying unit 34 is switched toward the defective article collection path R2.

Accordingly, a suction means (suction box 47, suction duct 48, suction source 49 and valve 50) is provided in the second embodiment.

This enables the absorbent article A1 guided by the first upstream conveying unit 34 to be reliably sucked to the circulating belt 45 by the suction means and conveyed along the defective article collection path R2 (sub path R7) by the second upstream conveying unit 35 even if the absorbent article A1 is conveyed at a high speed.

Note that although the upstream conveying mechanism 32 for guiding the absorbent article A1 to the defective article collection path R2 is described in the second embodiment, the upstream conveying mechanism 32 can be used to guide the absorbent article A1 to the sampling path R3 in the first embodiment.

On the other hand, the path switching means 5 for guiding the absorbent article A1 to the sampling path R3 in the first embodiment can also be used to guide the absorbent article A1 to the defective article collection path R2.

Further, although the upstream conveying units 34, 35 are respectively driven by the motors 51, 52 in the second embodiment, the upstream conveying units 34, 35 may be driven by a common motor.

Note that the specific embodiments described above mainly include inventions having the following configurations.

Specifically, the present invention provides a conveying device switchable between a state where an absorbent article is conveyed along a main conveyance path set in advance and a state where the absorbent article is conveyed along a branch conveyance path branched off from the main conveyance path, the conveying device including an upstream conveying mechanism provided on the main conveyance path and configured to convey the absorbent article, a downstream conveying mechanism provided downstream of the upstream conveying mechanism on the main conveyance path and configured to convey the absorbent article and a path switching means configured to switch a conveyance path of the absorbent article to guide the absorbent article to the branch conveyance path in the process of transferring the absorbent article from the upstream conveying mechanism to the downstream conveying mechanism, the path switching means including a belt conveying unit with a conveying belt arranged along an annular path and configured to circulate along the annular path so as to be able to convey the absorbent article and a path switching mechanism configured to switch a conveyance path specified by the conveying belt between a path along which the absorbent article is transferrable from the upstream conveying mechanism to the downstream conveying mechanism and a path along which the absorbent article is guided along the branch conveyance path from the upstream conveying mechanism.

According to the present invention, a conveyance destination of the absorbent article can be switched between the main conveyance path and the branch conveyance path by switching the conveyance path specified by the conveying belt with the conveying belt kept circulating.

Thus, unlike a case where a sorting member is rotated only during conveyance to the branch conveyance path as before, it can be suppressed that a speed difference is created between the conveying belt and the absorbent article during conveyance to the branch conveyance path, whereby frictional resistance given to the absorbent article can be reduced.

Therefore, according to the present invention, the absorbent article can be precisely sorted between the main conveyance path and the branch conveyance path.

In the conveying device, preferably, the path switching means includes a pair of switching conveyors provided between the upstream conveying mechanism and the downstream conveying mechanism on the main conveyance path, each switching conveyor includes the belt conveying unit and the path switching mechanism and the both path switching mechanisms are capable of switching directions of the both belt conveying units between a state where the absorbent article is conveyed along the main conveyance path while being sandwiched between the both conveying belts and a state where the absorbent article is conveyed along the branch conveyance path while being sandwiched between the both conveying belts.

According to this mode, the absorbent article can be conveyed to the main conveyance path or the branch conveyance path while being sandwiched between the pair of conveying belts.

Since this can more effectively reduce frictional resistance between the absorbent article and the both conveying belts, the damage of the absorbent article can be prevented.

Further, since the directions of the pair of belt conveying units themselves sandwiching the absorbent article are switched in the above mode, the absorbent article can be reliably conveyed along the main conveyance path or the branch conveyance path.

Note that although the path switching mechanisms (switching conveyors) are provided separately from the upstream conveying unit and the downstream conveying unit in the above mode, the upstream conveying unit may include the path switching mechanism.

Specifically, in the conveying device, the upstream conveying mechanism may include a first upstream conveying unit with the path switching means and a second upstream conveying unit configured to convey the absorbent article between the first upstream conveying unit and the second upstream conveying unit, the second upstream conveying unit may include a circulating belt arranged along an annular path for branching including a main path extending along the main conveyance path and an sub path extending along the branch conveyance path and configured to circulate along the path for branching and the path switching mechanism may be configured to switch the path specified by the conveying belt between a state where the absorbent article is conveyed along the main path while being sandwiched between the circulating belt and the path switching mechanism and a state where the absorbent article is guided to the sub path while being sandwiched between the circulating belt and the path switching mechanism.

According to the above mode, the path specified by the conveying belt of the first upstream conveying unit can be switched between a state where the absorbent article is conveyed along the main conveyance path (main path) between the first and second upstream conveying units and a state where the absorbent article is guided to the branch conveyance path (sub path) between the first and second upstream conveying units.

Thus, the configuration of the conveying device can be simplified and a cost reduction caused by this can be realized as compared to the case where the path switching mechanism is provided separately from the upstream and downstream conveying units.

In the conveying device, preferably, the annular path of the conveying belt includes a conveying path extending along the main conveyance path and the path switching mechanism includes a pressing member provided movably with respect to the conveying belt and a driving member configured to drive the pressing member with respect to the conveying belt between a position where a part of the conveying belt extending along the conveying path is pressed from an inner side of the annular path to guide the absorbent article to the sub path and a position where the conveying belt is released from pressing.

According to the above mode, the path specified by the conveying belt can be switched by the pressing of the conveying belt by the pressing member and the release from this pressing.

Note that the pressing member's "position where the conveying belt is released from pressing" means to include a position where the pressing member is in contact with the conveying belt within a range where the absorbent article is conveyed along the main conveyance path.

Here, if the absorbent article is conveyed at a high speed in the upstream conveying mechanism, the absorbent article moves toward the main conveyance path by inertia and it is difficult to convey the absorbent article along the branch conveyance path (sub path) even if the path specified by the conveying belt of the first upstream conveying unit is switched toward the branch conveyance path.

Accordingly, in the conveying device, the second upstream conveying unit preferably includes a suction means configured to suck the absorbent article located on a part of the circulating belt extending along the sub path toward the circulating belt.

According to the above mode, the absorbent article guided by the first upstream conveying unit can be reliably sucked to the circulating belt by the suction means and conveyed along the branch conveyance path (sub path) by the second upstream conveying unit even if the absorbent article is conveyed at a high speed.

Note that, out of absorbent articles conveyed by the conveying device, defective articles need to be conveyed to a collection site set in advance.

Accordingly, in the conveying device, the upstream conveying mechanism preferably further includes a defective article sorting unit configured to guide defective articles satisfying a defect condition set in advance out of the absorbent articles conveyed along the main conveyance path to a defective article collection path branched off from the main conveyance path.

According to the above mode, since the path switching mechanism is provided separately from the defective article sorting unit, it is possible to guide absorbent articles, except defective articles, required to be more carefully handled than the defective articles to the branch conveyance path with frictional resistance suppressed as described above while collecting the defective articles along the defective article collection path by the defective article sorting unit.

Specifically, the path switching means may further include a controller configured to control an operation of the path switching mechanism such that the absorbent article is guided to the branch conveyance path when the number of the absorbent articles, except the defective articles, conveyed by the upstream conveying mechanism reaches a preset number.

This enables one out of every preset number of the absorbent articles to be sampled and used, for example, for inspection to confirm a state of products.

Further, the present invention provides a conveyance method for conveying an absorbent article using the conveying device, the conveyance method including a main conveyance step of conveying the absorbent article along a main conveyance path set in advance and a branch conveyance step of conveying the absorbent article along a branch conveyance path branched off from the main conveyance path, a conveyance path specified by the conveying belt being set to be able to transfer the absorbent article from the upstream conveying mechanism to the downstream conveying mechanism with the conveying belt kept circulating in the main conveyance step, and the conveyance path specified by the conveying belt being set to guide the absorbent article along the branch conveyance path from the upstream conveying mechanism with the conveying belt kept circulating in the branch conveyance step.

According to the present invention, a conveyance destination of the absorbent article can be switched between the main conveyance path and the branch conveyance path by switching the conveyance path specified by the conveying belt with the conveying belt kept circulating.

Thus, unlike a case where a sorting member is rotated only during conveyance to the branch conveyance path as before, it can be suppressed that a speed difference is created between the conveying belt and the absorbent article during conveyance to the branch conveyance path, whereby frictional resistance given to the absorbent article can be reduced.

Therefore, according to the present invention, the absorbent article can be precisely sorted between the main conveyance path and the branch conveyance path.

The invention claimed is:

1. A conveying device switchable between a state where an absorbent article is conveyed along a main conveyance path set in advance and a state where the absorbent article is conveyed along a branch conveyance path branched off from the main conveyance path, the conveying device comprising:
   an upstream conveying mechanism provided on the main conveyance path and configured to convey the absorbent article, the upstream conveying mechanism including a first upstream conveying unit with a path switching means and the upstream conveying mechanism further including a second upstream conveying unit configured to convey the absorbent article between the first upstream conveying unit and the second upstream conveying unit, the second upstream conveying unit including a circulating belt arranged along an annular path for branching including a main path extending along the main conveyance path and a sub path extending along the branch conveyance path and configured to circulate along the path for branching;

a downstream conveying mechanism provided downstream of the upstream conveying mechanism on the main conveyance path and configured to convey the absorbent article; and the path switching means being configured to switch a conveyance path of the absorbent article to guide the absorbent article to the branch conveyance path in a process of transferring the absorbent article from the upstream conveying mechanism to the downstream conveying mechanism, the path switching means including a belt conveying unit with a conveying belt arranged along an annular path and configured to circulate along the annular path so as to be able to convey the absorbent article and a path switching mechanism configured to switch a conveyance path specified by the conveying belt between a path along which the absorbent article is transferrable from the upstream conveying mechanism to the downstream conveying mechanism and a path along which the absorbent article is guided along the branch conveyance path from the upstream conveying mechanism, the path switching mechanism being configured to switch the path specified by the conveying belt between a state where the absorbent article is conveyed along the main path while being sandwiched between the circulating belt and the conveying belt and a state where the absorbent article is guided to the sub path while being sandwiched between the circulating belt and the conveying belt;

the annular path of the conveying belt includes a conveying path extending along the main conveyance path;

the path switching mechanism includes a pressing member provided movably with respect to the conveying belt and a driving member configured to drive the pressing member with respect to the conveying belt between a position where a part of the conveying belt extending along the conveying path is pressed from an inner side of the annular path to guide the absorbent article to the sub path and a position where the conveying belt is released from pressing;

the upstream conveying mechanism further includes a defective article sorting unit configured to guide defective articles satisfying a defect condition set in advance out of the absorbent articles conveyed along the main conveyance path to a defective article collection path branched off from the main conveyance path; and the path switching means further includes a controller configured to control an operation of the path switching mechanism such that the absorbent article is guided to the branch conveyance path when the number of the absorbent articles, except the defective articles, conveyed by the upstream conveying mechanism reaches a preset number.

2. The conveying device according to claim 1, wherein the second upstream conveying unit preferably includes a suction means configured to suck the absorbent article located on a part of the circulating belt extending along the sub path toward the circulating belt.

3. A conveyance method for conveying an absorbent article using the conveying device according to claim 1, comprising:

operating the upstream conveying mechanism, the downstream conveying mechanism and the path switching means so that the absorbent article is conveyed along a main conveyance path set in advance; and operating the path switching means so that the absorbent article is conveyed along a branch conveyance path branched off from the main conveyance path;

operating the path switching means so that a conveyance path specified by the conveying belt being set to be able to transfer the absorbent article from the upstream conveying mechanism to the downstream conveying mechanism, and keeping the conveying belt circulating when operating the upstream conveying mechanism, the downstream conveying mechanism and the path switching mechanism; and operating the path switching mechanism so that the conveyance path specified by the conveying belt is set to guide the absorbent article along the branch conveyance path from the upstream conveying mechanism, and keeping the conveying belt circulating in the when operating the path switching means.

\* \* \* \* \*